United States Patent [19]
Calderon

[11] Patent Number: 4,714,460
[45] Date of Patent: Dec. 22, 1987

[54] METHODS AND SYSTEMS FOR RETROGRADE PERFUSION IN THE BODY FOR CURING IT OF THE DISEASE OR IMMUME DEFICIENCY

[76] Inventor: Reynaldo Calderon, 1202 Harvard, Houston, Tex. 77008

[21] Appl. No.: 871,528

[22] Filed: Jun. 6, 1986

Related U.S. Application Data

[63] Continuation of Ser. No. 518,685, Jul. 29, 1983, abandoned.

[51] Int. Cl.$^4$ .................................................. A61B 1/06
[52] U.S. Cl. ........................................ 604/28; 604/43; 604/53; 604/264
[58] Field of Search ............... 604/4, 8, 9, 27, 28, 604/30, 32, 33, 34, 39, 45, 52, 43, 53, 93, 151, 175, 248, 249, 256, 264, 284, 35, 41; 128/1 R, DIG. 3, 6

[56] References Cited

U.S. PATENT DOCUMENTS

| | | | |
|---|---|---|---|
| 3,435,824 | 4/1969 | Gamponia | 604/101 |
| 4,040,413 | 8/1977 | Ohshiro | 128/6 |
| 4,192,302 | 3/1980 | Boddie | 604/4 |
| 4,290,428 | 9/1981 | Durand, et al. | 604/96 |
| 4,448,188 | 5/1984 | Loeb | 604/96 |
| 4,459,977 | 7/1984 | Pizon et al. | 604/102 |

OTHER PUBLICATIONS

Ausman, et al., "Isolated Perfusion of the Liver with HN$_2$", Surgical Forum, 1959, vol. X, pp. 77-79.
Ausman, "Development of a Technique for Isolated Perfusion of the Liver", NY State Med. J., 1961, pp. 3993-3997.
Chung, et al., "A Technique of Isolated Perfusion of the Liver", Surgery 1962, vol. 51, No. 4, pp. 508-511.

*Primary Examiner*—C. Fred Rosenbaum
*Assistant Examiner*—Sherri E. Vinyard
*Attorney, Agent, or Firm*—Pravel, Gambrell, Hewitt, Kimball & Krieger

[57] ABSTRACT

Catheter feedback methods and systems are disclosed for optimizing the infusion of a drug, such as a chemotherapeutic agent via retrograde perfusion through the venous side of the vascular network to a selectively determined portion of a solid tumor. Monitoring and regulatory capability are provided for controlling the outflow of the drug and thereby for controlling the dose rate, the duration of exposure of the drug, the leakage factor, and the level of systemic toxicity, all critical factors in the successful treatment of solid tumors. A feedback loop for practicing the method comprises two concentric balloon catheters capable of extensive maneuvering and selective placement within the venous drainage of the vascular system, creating a third in-vivo space for repeated perfusion of the selected portion of a diseased organ as often as desired, providing maximum exposure of the chemotherapy to the tumor with minimum exposure to any other portions of the patient's body.

12 Claims, 6 Drawing Figures

METHODS AND SYSTEMS FOR RETROGRADE PERFUSION IN THE BODY FOR CURING IT OF THE DISEASE OR IMMUNE DEFICIENCY

This is a continuation of application Ser. No. 518,685 filed July 29, 1983 now abandoned.

BACKGROUND OF THE INVENTION

In the conventional treatment of a solid tumor, the state of the art lies in arterial infusion, a one-way process which comprises a single pass of a chemotherapeutic agent via the arterial side of the body through the tumor. The principal drawback to this method is the inability to maintain the dose rate and/or duration of exposure of a drug necessary to effect a response, due to the resulting systemic toxicity. That is, with present methods, the successful treatment of a solid tumor with chemotherapy is undermined by leakage of the chemotherapy which proves detrimental to the remainder of the body.

Routine blood flow originates in the heart and progresses in an arterial to capillary to venous sequence. The walls of the post-capillary venules, capillaries, and sinusoids are exchange vessels, serving as the site of exchange between the blood and the tissue bathing the cells. The larger venules and veins comprise a system of capacitance or reservoir vessels. These are large-volume, low-pressure vessels through which the cardiac (right side of the heart) return occurs.

Under normal conditions, the endothelial cells that form the lining of the vascular network renew themselves very slowly. According to Folkman, in an article entitled "The Vascularization of Tumors." *Scientific American*, June, 1976, (p. 71) "Occasionally there is a brief burst of proliferative activity in one part of the vascular system when such activity is needed to heal a wound or mount an immune response. However, the new vessels always regress after a short time, and regenerative activity subsides to its former low state." The cells proliferate rapidly where needed for the purpose of immunity as of healing wounds. However, such proliferation is maintained only as long as necessary. Thereafter, regenerative activity assumes its former state.

Blood circulation to a solid tumor likewise flows routinely from arterial to capillary to venous. However, in the topographical region between the exchange vessels and the larger venules, the direction of flow changes dramatically. Folkman explains what occurs: "When a malignant tumor sends out its chemical message, the proliferation of endothelial cells rises steeply in the vicinity of the tumor. Capillaries bud from the side walls of venules and lengthen into thin tubes, converging on the tumor from all directions." This characteristic of the tumor vessels results in the creation of numerous venous-venous (V-V) shunts, which are the physical elements that underlie the process of retrograde perfusion. The significance of the V-V shunts in the treatment of tumors is explained as follows.

The normal driving pressure in the tumor vasculature is the change in velocity of the blood flowing from the capillary into the venous system by means of the cross-sectional area ($V \times A_{capillaries} = V \times A_{venous}$) That is, the pressure drop across these V-V channels is created by the change in velocity of the blood flow as it emerges from the capillaries. The tumor blood flow is thus impaired, measuring only two to fifteen percent of that of the surrounding tissue, and this impaired circulation distinguishes the cancer vasculature. The probability of blood flow through the V-V shunts is far less than the probability of blood flow through the normal vasculature. Therefore, in any attempt to deliver chemotherapy to a tumor, the likelihood that the drug will spread to the remainder of the body is far greater than the likelihood that it will reach the tumor.

Systemic toxicity resulting from chemotherapeutic regimens remains an obstacle to the successful treatment of cancer. In 1961, Stehlin, et. al. identified leakage of the chemotherapeutic agent into the systemic circulation as "one of the most serious limitations as to the success of perfusion of certain regions of the body." As recently as March, 1981, the *Journal of the American Medical Association* featured an article by Kato, et. al. and a related editorial by Chuang addressing chemoembolization, which is the "combination of arterial infusion of a chemotherapeutic agent and arterial embolization of the vascular supply to a neoplasm." This method produced a prolonged survival rate; however, the dosage rate was limited by systemic toxic effects. Similarly, in all of the techniques outlined by Fewer, Wilson, and Lewis, the outflow returning to the venous system was left unaltered, resulting in systemic toxicity and a failure to maintain the needed duration of exposure of the drug. Dosage rate is another critical factor in cancer chemotherapy. Evidence supports the conclusion that maintenance of high doses of anti-tumor therapy substantially increases the response rate. This can be noted in marrow transplants, isolation infusion, or regional perfusion studies. Yet, arterial perfusion and infusion into the solid tumors have demonstrated that the first passage of the drug in those methods is the only advantage over intravenous (IV) injection; thereafter toxicity remains the same.

SUMMARY OF THE INVENTION

Systemic toxicity and dosage are critical factors in treating solid tumors; however, it is possible that previous techniques have been unsuccessful because of a failure to consider the significance of two other factors: one, the V-V shunts typical of the tumor vaculature, and two, the outflow draining from the tumor. The key to successful perfusion lies in exploiting and incorporating the tumor vasculature and in controlling its outflow, and retrograde perfusion according to the present invention provides a mechanism for achieving both of those objectives.

The present invention is illustratively described as comprising two concentric catheters with extensive maneuverability as well as pumps, filters, analyzers, and other suitable means for regulating and monitoring the outflow draining from the tumor. The initial step is to take an arteriogram which yields a graphic representation of the internal loops within the blood flow and aids in determining the preferential drainage. The perfusion process begins with retrograde insertion of the two concentric catheters into the preferential drainage of a solid tumor via an external vein. One catheter marks the site of entry of the chemotherapeutic agent and provides access to the V-V shunt. The second, or suction, catheter is placed distally and has the suction capacity necessary to accommodate the therapeutic input, the arterial blood flow, the venous and lymphatic drainage, and the preferential drainage. Next, with the catheters in position, retrograde emboli are placed in critical areas of the vasculature to inhibit leakage. The treating physician may make corrections or adjustments needed during treatment because of the changing cross-sectional areas, the impaired circulation, and other factors characteristic of the tumor vasculature.

The concentric catheters placed within the tumor preferential drainage as described above form a third in-vivo space in addition to the first (cells) and second (interstitial spaces around the cells) in vivo spaces. It is here that the procedure differs from previous methods. Within the selected area of an organ chosen for perfusion, a feedback loop has been formed with exterior access to a monitoring system which monitors pressure, concentration, temperature, time, and other variables to insure that systemic toxicity is avoided, that an appropriate dose rate is maintained, and that the integrity of the organ is not violated. As the drug is perfused through the solid tumor, it is bio-transformed responsive to the conditions of at least one and preferably all three of the body, the tumor, and the spent drug itself. Next, it is led out of the body via the suction catheter to be filtered and analyzed by suitable filter and analyzer means. Then, the process is repeated as often as necessary until the desired steady state is achieved. Retrograde perfusion according to the present invention thus provides a treatment technique which succeeds in effect in establishing the clinician as an element of the tumor vasculature. From this vantage point, the clinician is able to interact with the tumor and see what the possibilities of interaction are, becoming a monitor of the tumor's evolutionary process and thus capable of feedback system with virtually unlimited interaction possible.

The present invention is characterized by three features commonly lacking in previous methods of treatment. First, previous methods fail to change the basic pattern of the established blood flow in the tumor. Second, previous methods allow the established cancer cells to persist, never interrupting the homeostatic inertia of the tumor. Finally, because previous methods lack the capability of interacting with the tumor, they are incapable of controlling the flow pattern and thus the duration of exposure, dose rate, preferential drainage, leakage factor, and level of toxicity which are crucial in the successful treatment of cancer.

One advantage of the present method is that it recognizes the significance of the V-V shunt, but no longer treats vascular flow through the V-V shunt as a substrate limited process. The physical structure of the tumor vasculature is a limiting factor in the delivery of chemotherapy. By the nature of their location beyond the pre-capillary sphincter and the capillary beds, the V-V shunts can be perfused only randomly by present methods—concentration, duration of exposure, in short, bioavailability of chemotherapy is random. With retrograde perfusion it will no longer be necessary to reckon with the impaired circulation through the tumor, for the new method will enable the clinician to provide chemotherapy at a pressure rate needed to drive the flow backward through the loop created in the tumor vasculature. Because the loop has been created such that leakage sites are blocked, systemic toxicity is avoided, yet adequate levels of chemotherapy are certain to reach the tumor.

A second advantage of retrograde perfusion is that it recognizes the importance of tumor progression, which is the steady increase in malignancy characteristic of vascularized tumors. According to Folkman, tumor progression is a result of the rapid increase in cell division caused by vascularization. As cells proliferate over a period of time, they at first metastasize, then invade surrounding tissue, and finally, appear as ascites cells in the host's abdominal cavity. The present method appreciates the different stages of tumor progression and allows the clinician to intervene selectively at the appropriate time with the appropriate combination of dose rate, concentration, pressure, duration of exposure, and other factors which will inhibit vascularization with subsequent tumor growth.

The dose response curve of chemotherapeutic agents is well known; the more effective the drug, the steeper the curve. Presently, dose response is measured by three criteria—reduction in tumor mass, increased survival, or bioassay methods. A third advantage of retrograde perfusion is that it permits optimum assessment of the steep dose response curve, particularly by the bioassay method. By closely tracking the dose response, every effort is made to eliminate the deflection point which represents tumor growth and decreased patient survival.

Another advantage of the present method is that it virtually separates the tumor from the body. Division of the tumor load from the host provides opportunities in several ways. It heightens the immune system; it eliminates the single pass of chemotherapy typical of arterial perfusion; it provides constant contact of the chemotherapeutic agent within the tumor vessels, which is particularly useful with a radio-sensitizing agent; and it facilitates delivery of a radioactive slurry via the catheter system. Furthermore, the chemotherapy can be calculated on the basis of tumor burden rather than being limited by the effects of the systemic toxicity, and the concentric catheters can be utilized as an access point for hyperalimentation to induce patient well-being.

The last and most significant advantage of retrograde perfusion according to the present invention is that it can be applied not only to the delivery of any chemotherapeutic regimen but to numerous other aspects of treatment.

DESCRIPTION OF PREFERRED EMBODIMENT

Figure 1:
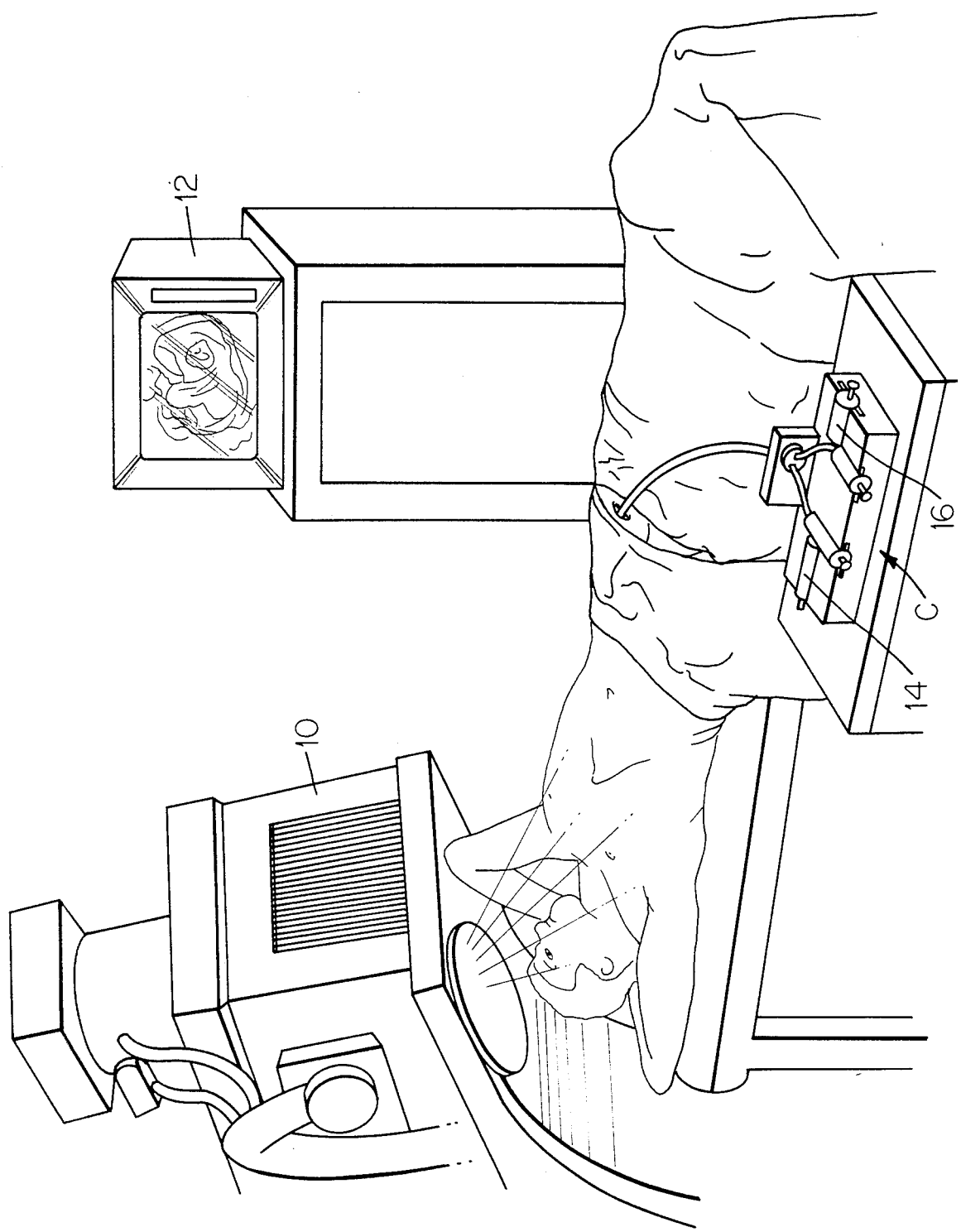
FIG. 1 is an isometric view of a patient undergoing treatment.
Figure 6:
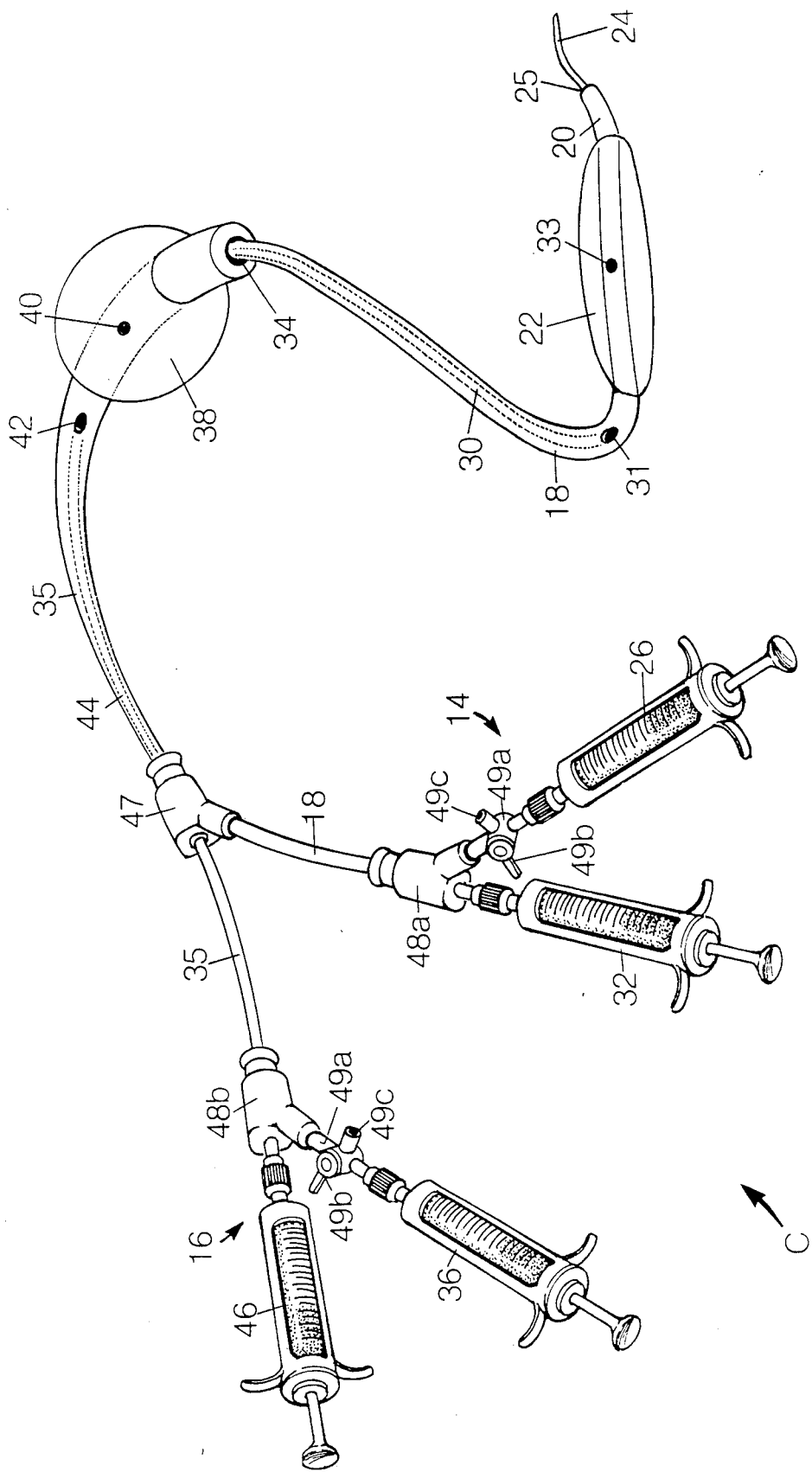
FIG. 6 is an isometric view of a double balloon, concentric catheter according to the present invention.

According to the present invention, a double balloon concentric catheter system C (FIGS. 1 and 6) is used to treat a person. The catheter C is used for retrograde perfusion of a patient's body, by which is meant that an agent is injected into the patient's venous system in a direction counter to normal blood flow. The retrograde injected agent then perfuses a portion of the body being treated via the venous system.

In a preferred embodiment, the catheter system C is used to inject and retrograde perfuse a therapeutic agent, a chemotheraputic agent for example, to a solid tumor in such a way that variables, such as the cidal concentration, duration of exposure and systemic toxicity may be controlled. As hereinafter set forth, the catheter system C can also be used for retrograde perfusion of an activating agent into a patient, such as an enzyme, catalyst, or an immunizing or immunological agent.

During treatment according to the present invention, the patient's response and reactions are observed and monitored by a computerized axial tomography (CAT) scanner 10 (FIG. 1) and a video monitor 12, using two double balloon concentric catheters 14 and 16. The double balloon concentric catheters 14 and 16 according to the present invention include an inner tube or infusion catheter 18 (FIG. 6) encircled near an end or tip 20 by an inflatable balloon 22 which is used to seal a patient's vein in which the catheter 18 is placed. The catheters 14 and 16 are shown in somewhat simplified form in FIG. 6 in order that structural features may more clearly be seen. The infusion catheter 18 is used on insertion to direct the flow of the therapeutic input fluid through vessels in the portion of the body being treated. As is usual, a guide wire 24 is provided in the end 20 of catheter 18 to assist in insertion and movement to the desired location in the patient's venous system. The guide wire 24 is withdrawn once the catheter 18 is properly positioned.

Driving power for the infusion catheter 18 is provided by a syringe injector 26 with push/pull capacity to insert and withdraw the catheter 18 which aids in establishing a feedback loop of flow beginning in the tumor vessels and extending outside the body, making it possible to control the concentration, pressure, temperature, and time duration of the therapeutic input. In this manner systemic toxicity is avoided, an appropriate dose rate is maintained, and the integrity of the organ is not violated. The infusion catheter 18 further includes an opening passage 25 in the end 20, forming a site of entry of the therapeutic input fluid into the patient's vein from the syringe 26. The infusion catheter 18 has an additional passageway or lumen 30 formed therein which may be used for either infusion or suction purposes. A port 33 is located within an area inflation of the balloon 22 as desired for sealing the veins and directing the flow of the chemotherapeutic agent. A port 31 is formed in the catheter 18 as an inlet to lumen 30 behind the inflatable balloon 22 and permits injection or extraction of fluid from the vein by a push/pull syringe injector 32.

A port 34 in a suction catheter 35 serves to collect partially or wholly spent chemotheraputic agent in a collector syringe 36 after it has been retrograde perfused through the tumor vessels, as hereinafter set forth. The infusion catheter 18 is concentrically mounted in the suction catheter 35, which functions to transport the collected agent outside the body to a collection syringe 36, from which fluid may be transferred to a suitable filter for filtration purposes. The filtered, toxic-free chemotherapy may then be re-injected as often as desired into the veins via port 25, thereby maintaining a continual feedback loop of flow essential for control of the variables mentioned above.

The second catheter 35 of the present invention also includes a balloon 38 which is inflatable in the patient's vein via a port 40 to seal the vein, blocking the flow of chemotherapeutic agent to the remainder of the patient's body. A port 42 is formed in catheter 35 providing access to a lumen or passageway 44 in fluid communication with a syringe injector 46. Syringe injector 46 contains the filtered flow free of toxicity which is circulated back into the venous system and the right side of the heart via port 42.

Catheters 18 and 35 are joined and made concentric at a T-junction or side arm 47. Similarly, the fluid passages to syringes 26 and 32 branch and remain separate so their fluids do not mix at a side arm 48a, while side arm 48b branches the fluid passages to syringes 36 and 46, keeping their respective fluids separate and distinct. Each of syringes 26 and 36 are provided with a tee member 49a controlled by lever 49b and having a sample port 49c.

The process of retrograde perfusion according to the present invention is performed in the following manner. Initially, the tumor vasculature is subjected to a conventional arteriogram with a dye or like agent for the purpose of mapping a selected portion of the tumor blood vessels, such as those shown at 50 (FIG. 3) in a tumor 52 in a kidney 54. The arteriogram effects a result known as tumor blush which aids in locating the tumor vessels 52 and a preferential drainage route 56. The image of the tumor vessels 52 and preferential drainage 56 is projected into the video screen 12 with the help of the scanner 10. Having completed the preliminary steps described above, positioning of the catheters 18 and 35 within the vasculature is begun.

Figure 2:
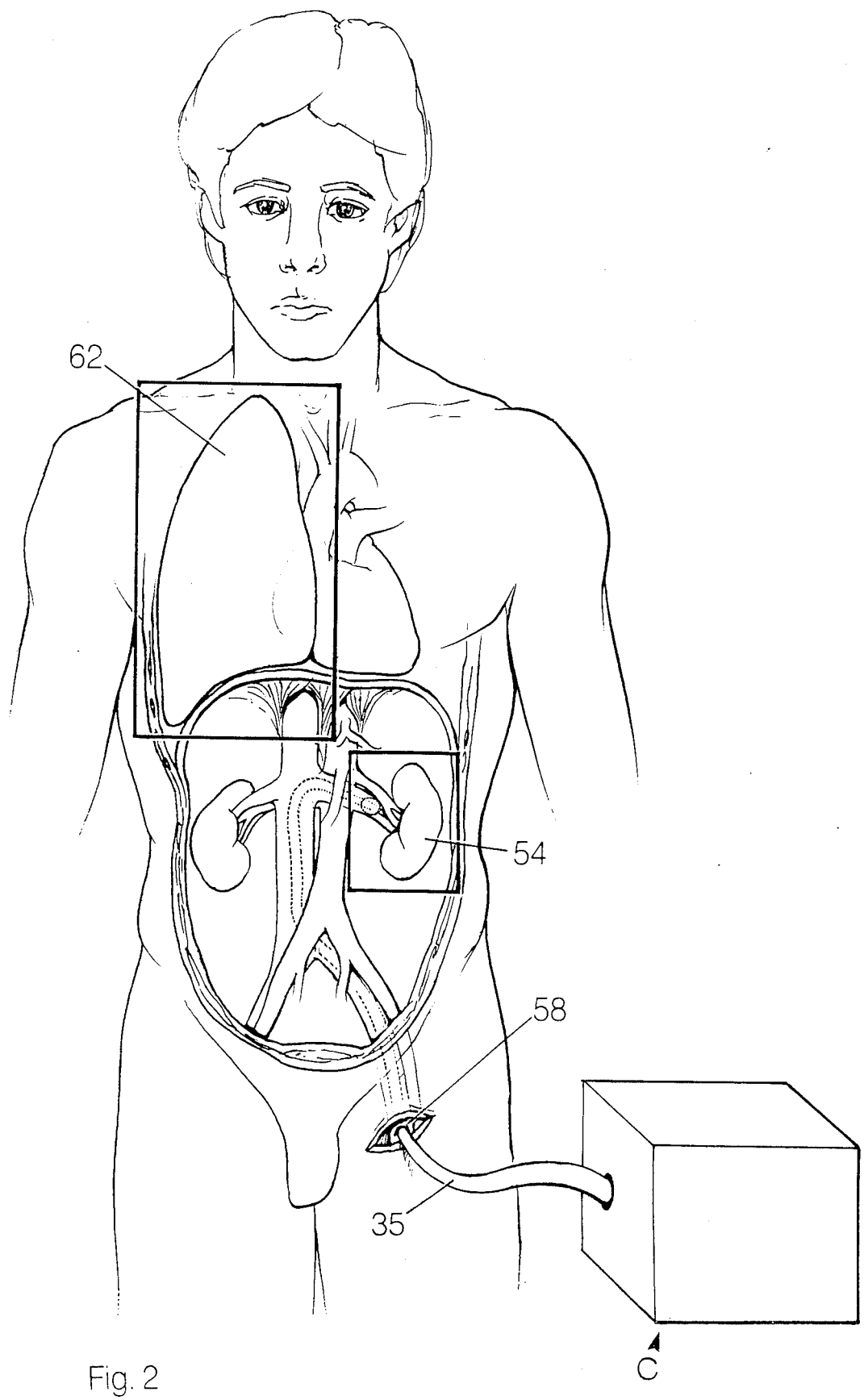
FIG. 2 is a schematic view of treatment of a kidney according to the present invention.
Figure 3:
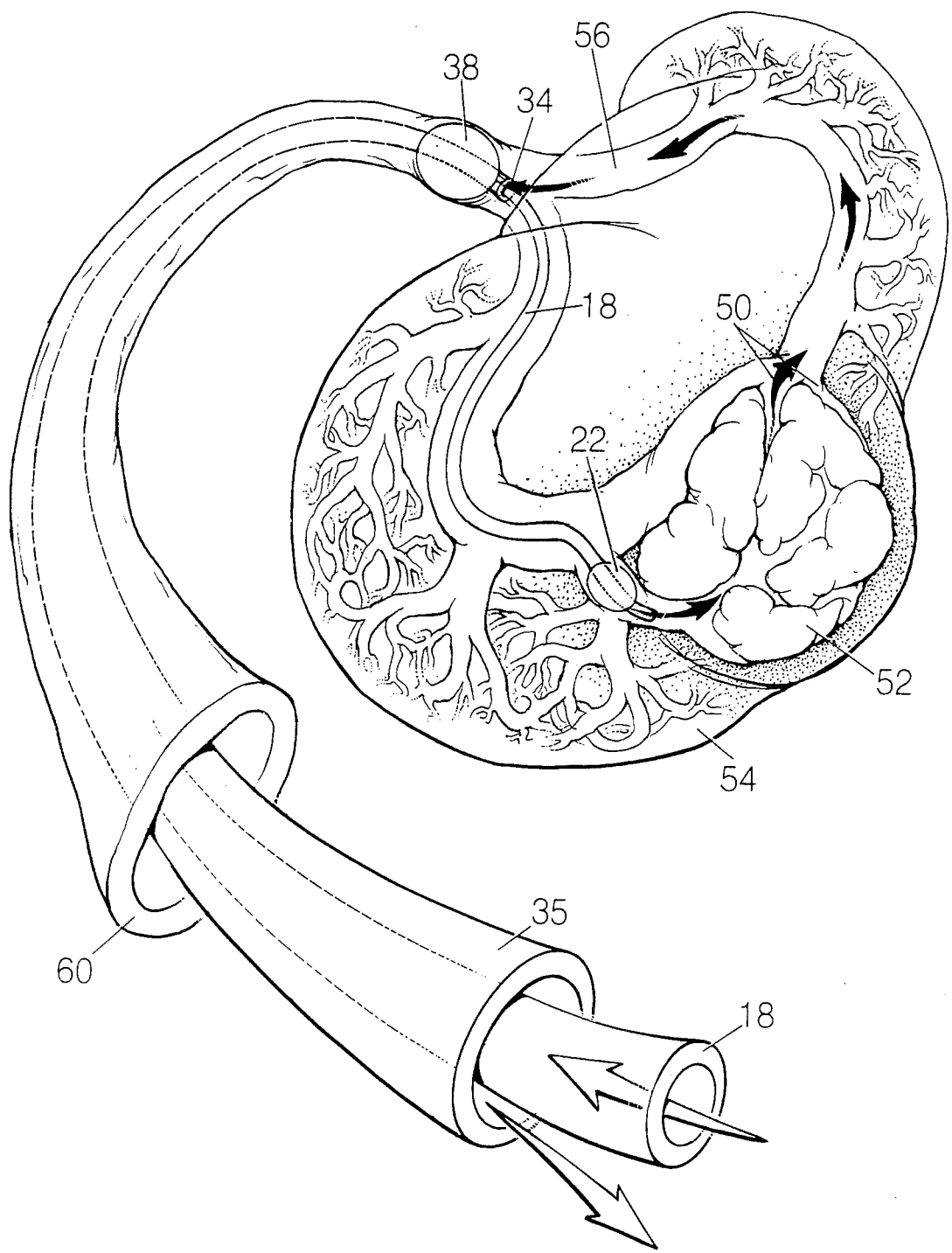
FIG. 3 is an enlarged schematic view of the kidney being treated in FIG. 2.

The concentric catheters 18 and 35 access to an organ, for example the left kidney 54 (FIG. 2), is via left femoral vein 58 into the left renal vein 60 (FIG. 3). To manipulate the concentric catheters 18 and 35 such that their appropriate placement is insured, the image on video screen 12 and the guide wire 24 are used. The guide wire 24 guides the catheter 18 through the left femoral vein 58 to the appropriate site in the renal vein 60, identified as the preferential drainage, where the suction catheter 35 is able to collect the outflow from the tumor. When proper placement of the suction catheter 35 is achieved, the guide wire 24 is extracted from within the suction catheter 35 while the catheter 35 remains in place. The same procedure is followed in placing the second, or infusion, catheter 18 in the site selected for perfusion of the kidney.

Figure 4:
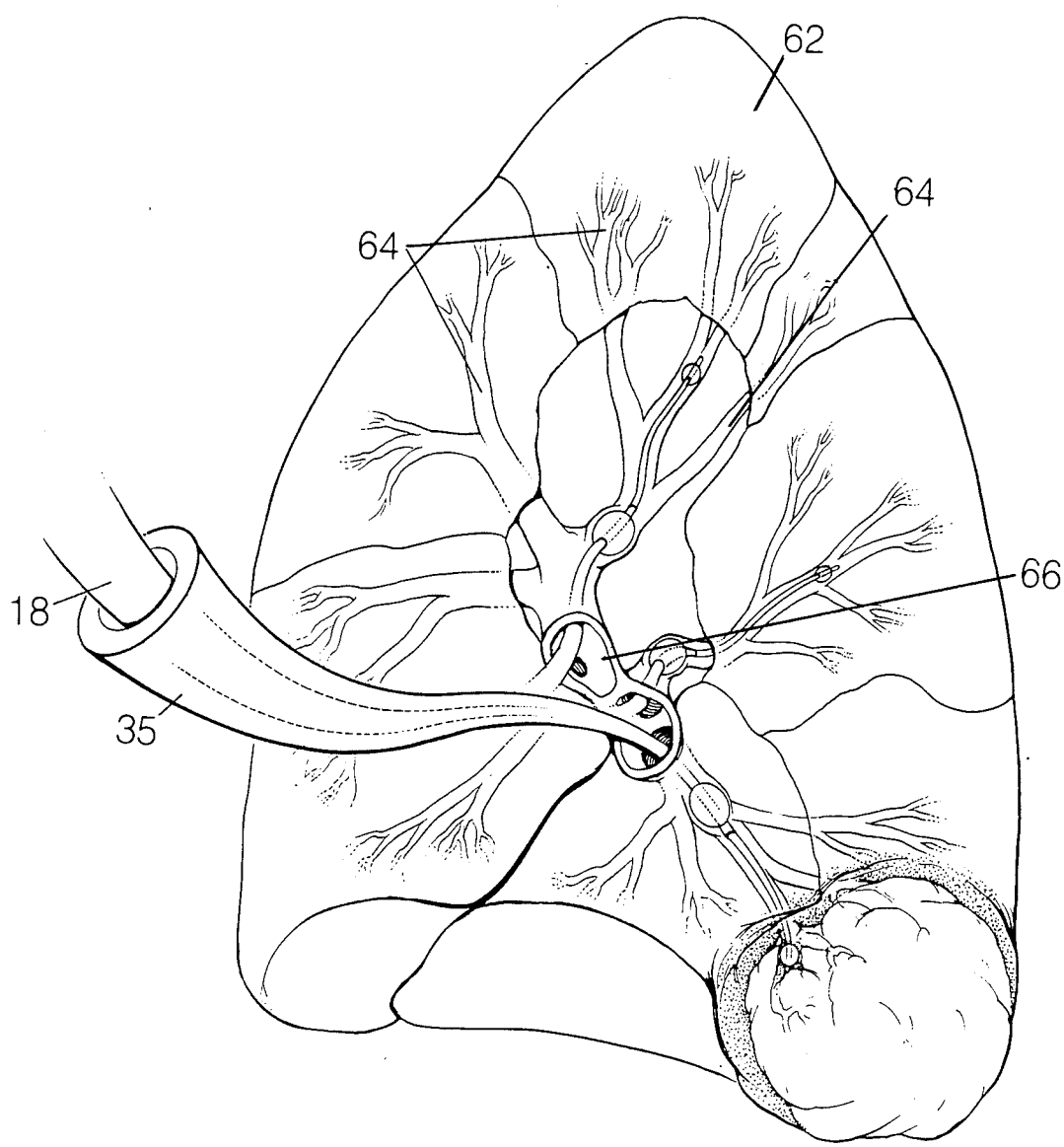
FIG. 4 is an enlargement of a lung being treated according to the present invention.

FIG. 4, depicting the right lung 62 with multiple tributaries 64 draining into the large pulmonary veins 66, illustrates the extensive maneuverability of catheters 18 and 35 which may be relocated as often as desired and in as many sites as desired within the vasculature of said place, if desired, retrograde embolization of selected blood vessels can be performed to isolate a particular venous flow path. To accomplish this step, a microencapsulated agent that degrades on demand or that can be retrieved as desired can be placed selectively within the branches of the blood vessels which are to be excluded from the perfusion process. This forms the third in-vivo space and isolates the V-V shunts past the tumor being treated. Embolization of the veins in this manner helps eliminate leakage of the therapeutic agent to other areas of the body and helps establish a direction for the flow of the agent. After the balloons 22 and 38 of catheters 18 and 35 are inflated (FIG. 5) and emboli are in place, and prior to actual perfusion with a chemotherapeutic agent, a simulation perfusion may be attempted in order to test the system for possible leakage sites or other problems. When all factors have been taken into consideration and the necessary adjustments made, the process of retrograde perfusion is initiated as the syringe injector 26 forces the therapeutic agent upstream into the vein 50, through the V-V shunts and along the path created by the inflated balloons 22 and 38 of catheters 18 and 35, and the emboli.

It is to be noted that the retrograde perfusion occurs for a substantial distance through the organ or portion of the patient's body being treated. As used with the present invention the term substantial difference is intended to mean that the balloons 22 and 38 are spaced from each other a distance to insure adequate flow of the agent through the tumor vasculature.

Figure 5:
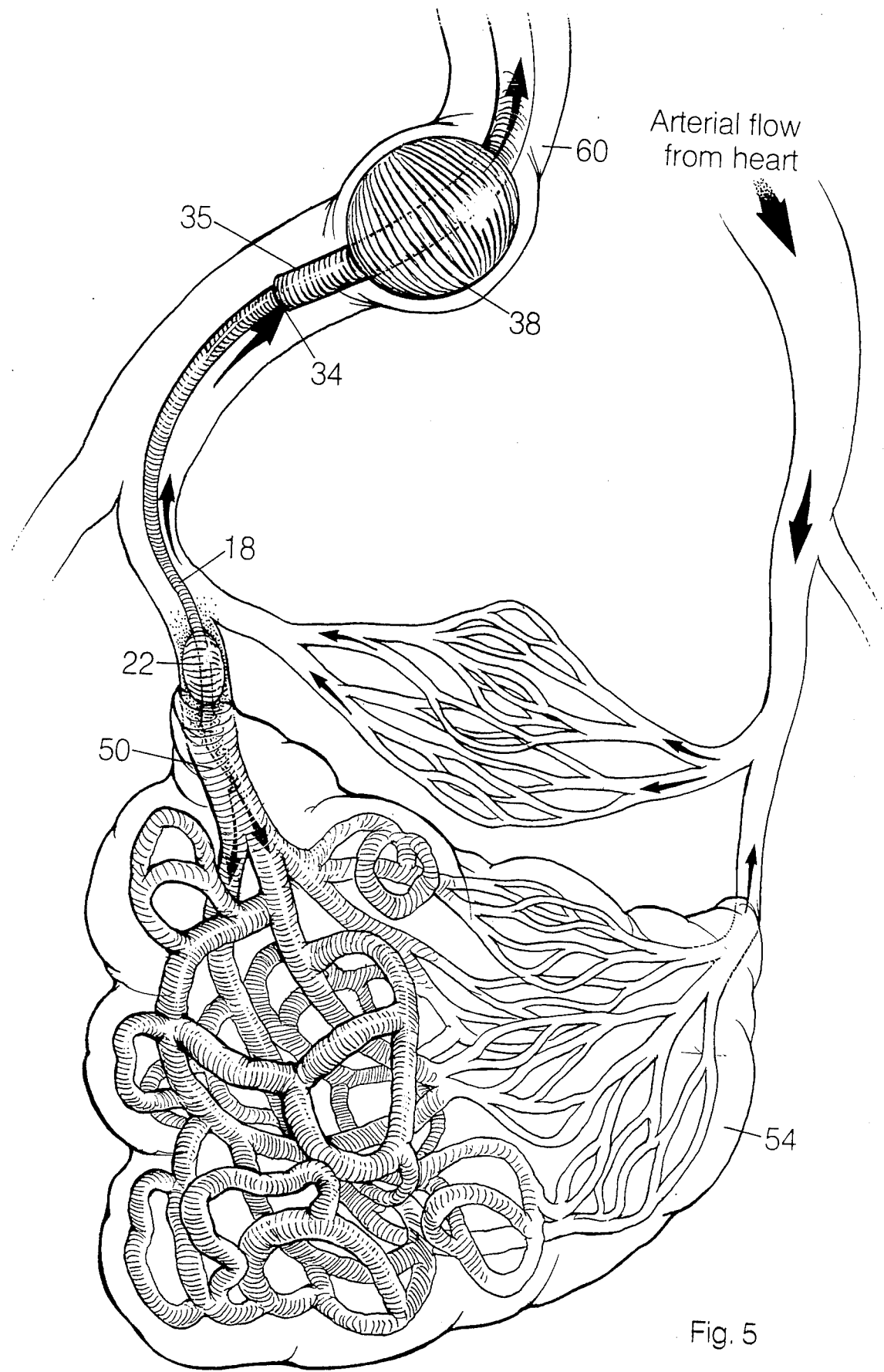
FIG. 5 is a schematic view of a catheter according to the present invention located in tortuous tumor vasculature.

The rate of infusion of chemotherapeutic agent by injector 26 in the tumor vasculature and extraction by injector 36 are kept equal so that no fluid can be forced contraflow to arterial flow (FIG. 5). Typically a number 20 of parallel V-V shunts are selectively formed for passage of agent through the tumor (FIG. 5) and no need for emboli exists due to equalized injection and extraction flow rates. However, emboli are available if needed.

The first feedback loop or passage of treating agent through the third in-vivo space is completed as the chemotherapy is drawn back into the suction catheter 35 via port 34 by means of syringe injector 36. The chemotherapy agent is then subjected to filtration and thereafter is reinjected via injector 26 and port 25 into the tumor vessels for repeated perfusion providing maximum exposure of the agent to the tumor and minimum exposure to the body. A feedback loop such as the one described above may be repeated as often as desired until the necessary balance of flow and desired homeostasis are achieved.

A second feedback loop is created as syringe injector 26 forces the chemotherapy or like agent upstream into the vein 50 through the V-V shunts and along a path created by the inflated balloons 22 and 38 of catheters 18 and 35 toward syringe injector 36 which draws the agent through port 34 for analysis and filtration purposes. Thereafter the filtered flow is directed by syringe 46 into the venous system and the right side of the heart via lumen 44 and port 42. Because the second feedback loop permits recirculation of the filtered flow to the rest of the body, it serves as an excellent means of hyperalimentation or stimulation for the body while the other feedback loop acts upon the tumor.

Separation of the tumor load from the body in this manner creates a third in-vivo space wherein the clinician may freely act upon and interact with the tumor. Because of the degree of control this invention provides, the two feedback loops may be implemented simultaneously and may be repeated indefinitely until the desired steady state is achieved in both loops. The therapeutic benefit of the dual feedback loop system for perfusion described herein is not limited solely to the treatment of solid tumors but may be applied as well as a means of hyperalimentation to induce patient well-being and as a means of providing an immunity or activating agent to a body deficient thereof.

It should also be recognized that a single catheter might, in certain situations be used for retrograde perfusion. In these instances, port 25 serves the point of injection ahead of balloon 22, while port 31 serves as the suction or extraction port. As has been set forth, the rates of injection and extraction are maintained equal.

The foregoing disclosure and description of the invention are illustrative and explanatory thereof, and various changes in the size, shape and materials, as well as in the details of the illustrated construction may be made without departing from the spirit of the invention.

I claim:

1. A method for treating a tumor in the body of a patient, comprising the steps of:
   (a) placing a catheter having a suction lumen and an infusion lumen extending beyond the suction lumen and a seal associated with each of such lumens in a vein of the patient near the tumor;
   (b) sealing the flow of fluid in the patient's vein between the infusion lumen and the suction lumen with the infusion seal;
   (c) sealing the flow of fluid in the patient's vein past the suction lumen with the suction seal;
   (d) injecting a chemotherapeutic agent from the infusion lumen into the patient's vein so that it may perfuse through the tumor; and
   (e) collecting the chemotherapeutic agent in the suction lumen after perfusion through the tumor.

2. The method of claim 1, further including the step of:
   analyzing the collected chemotherapeutic agent.

3. The method of claim 1, further including the step of:
   filtering the collected chemotherapeutic agent.

4. The method of claim 3, further including the step of:
   re-injecting the filtered chemotherapeutic agent into the vein of the patient.

5. The method of claim 1, further including the step of:
   maintaining the rate of collection substantially equal to the rate of injection.

6. The method of claim 1, further including the step of:
   mapping a selected portion of the tumor blood vessels prior to said step of placing the catheter.

7. The method of claim 1, further including the step of:
   testing the patient's venous system for possible leakage past the suction seal prior to said step of injecting a chemotherapeutic agent.

8. A catheter apparatus for treating a tumor in the body of a patient with a chemotherapeutic agent, comprising:
   (a) catheter means for location in a vein of the patient near the tumor, said catheter means comprising:
      (1) a suction lumen; and
      (2) an infusion lumen extending beyond said suction lumen;
   (b) infusion seal means on said catheter means between said infusion lumen and said suction lumen;
   (c) suction seal means on said catheter means for sealing the flow of fluid in the patient's vein past said suction lumen;
   (d) means for injecting a chemotherapeutic agent into the patient's vein from said injection lumen so that it may perfuse through the tumor; and
   (e) means for collecting the chemotherapeutic agent from said suction lumen after perfusion through the tumor.

9. The apparatus of claim 8, further including:
   means for analyzing the collected chemotherapeutic agent.

10. The apparatus of claim 8, further including:
    means for filtering the collected chemotherapeutic agent.

11. The apparatus of claim 12, further including:
    means for re-injecting the filtered chemotherapeutic agent into the vein of the patient.

12. The apparatus of claim 8, further including:
    means maintaining the rate of collection at said suction lumen substantially equal to the rate of injection at said injection catheter means.

* * * * *